US00PP25436P3

(12) United States Plant Patent
Shaw et al.

(10) Patent No.: US PP25,436 P3
(45) Date of Patent: Apr. 14, 2015

(54) STRAWBERRY PLANT NAMED 'MERCED'

(50) Latin Name: ***Fragaria×ananassa* Duch.**
Varietal Denomination: Merced

(71) Applicant: The Regents of the University of California, Oakland, CA (US)

(72) Inventors: Douglas V. Shaw, Davis, CA (US); Kirk D. Larson, Santa Ana, CA (US)

(73) Assignee: The Regents of the University of California, Oakland, CA (US)

( * ) Notice: Subject to any disclaimer, the term of this patent is extended or adjusted under 35 U.S.C. 154(b) by 107 days.

(21) Appl. No.: 13/986,425

(22) Filed: Apr. 30, 2013

(65) Prior Publication Data

US 2014/0325716 P1 Oct. 30, 2014

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Kilpatrick Townsend & Stockton LLP

(57) ABSTRACT

'Merced' is a short-day (June bearing) type cultivar that produces fruit over an extended period when treated appropriately in arid, sub-tropical climates. When treated with appropriate planting regimes, 'Merced' is similar to 'Camarosa' (U.S. Plant Pat. No. 8,708), but with greater productivity, higher quality fruit, less vigorous plant, and lighter colored fruit. It is also similar to 'Ventana' (U.S. Plant Pat. No. 13,469) and 'Benicia' (U.S. Plant Pat. No. 22,542) but having a more compact plant, later fruiting, superior fruit quality, and firmer, better flavored fruit.

5 Drawing Sheets

Genus and species: The strawberry cultivar of this invention is botanically identified as *Fragaria×ananassa* Duch.

Variety denomination: The variety denomination is 'Merced'.

BACKGROUND OF THE INVENTION

This invention relates to a new and distinctive short-day type cultivar designated as 'Merced'. The new cultivar was the result of a cross performed in 2007 between two unreleased germplasm accessions, Cal 3.92-8 (unpatented) and Cal 2.95-4 (unpatented). Accession Cal 3.92-8 was chosen as a parent due to its very high productivity, large, firm, and high quality fruit, and very high plant vigor. Accession Cal 2.95-4 was chosen as a parent due to its compact plant habit and firm, flavorful fruit.

'Merced' was first fruited at an experimental orchard near Winters, Calif., in 2008, where it was selected, originally designated Cal 7.132-3, and propagated asexually by runners. Following selection and during testing, the plant of this selection was designated 'C229'. It was later designated 'Merced' for introduction into commerce and for international registration and recognition. Asexual propagules from this original source have been tested at facilities in Watsonville, Calif., in Irvine, Calif., and to a limited extent in grower fields starting in 2009. The cultivar is stable and reproduces true to type in successive generations of asexual reproduction.

BRIEF SUMMARY OF THE INVENTION

'Merced' is a short-day (June bearing) type cultivar that produces fruit over an extended period when treated appropriately in arid, sub-tropical climates. When treated with appropriate planting regimes, 'Merced' is similar to 'Camarosa' (U.S. Plant Pat. No. 8,708), but with greater productivity, higher quality fruit, less vigorous plant, and lighter colored fruit. It is also similar to 'Ventana' (U.S. Plant Pat. No. 13,469) and 'Benicia' (U.S. Plant Pat. No. 22,542) but having a more compact plant, later fruiting, superior fruit quality, and firmer, better flavored fruit.

BRIEF DESCRIPTION OF THE DRAWINGS

The figures depict various characteristics of the 'Merced' cultivar.

DETAILED DESCRIPTION OF THE INVENTION

Figure 1:
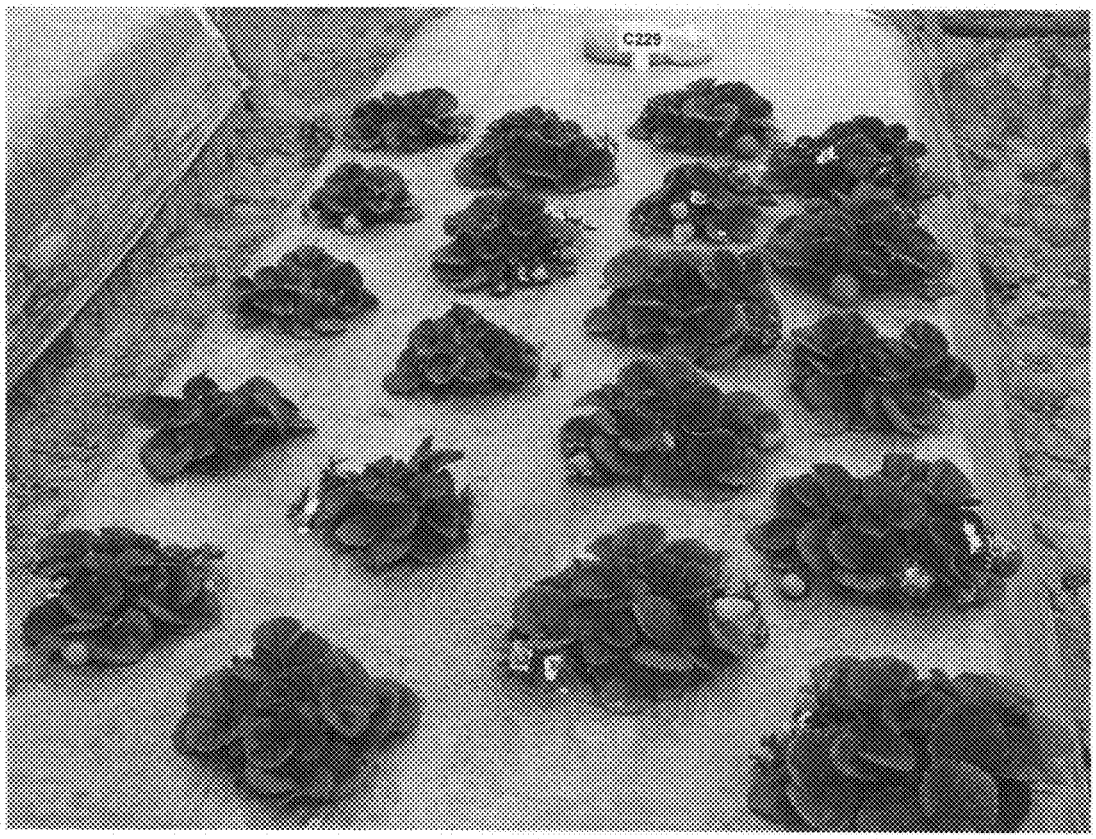
FIG. 1 shows the general flowering and fruiting characteristics of the plant in a field planting.
Figure 2:
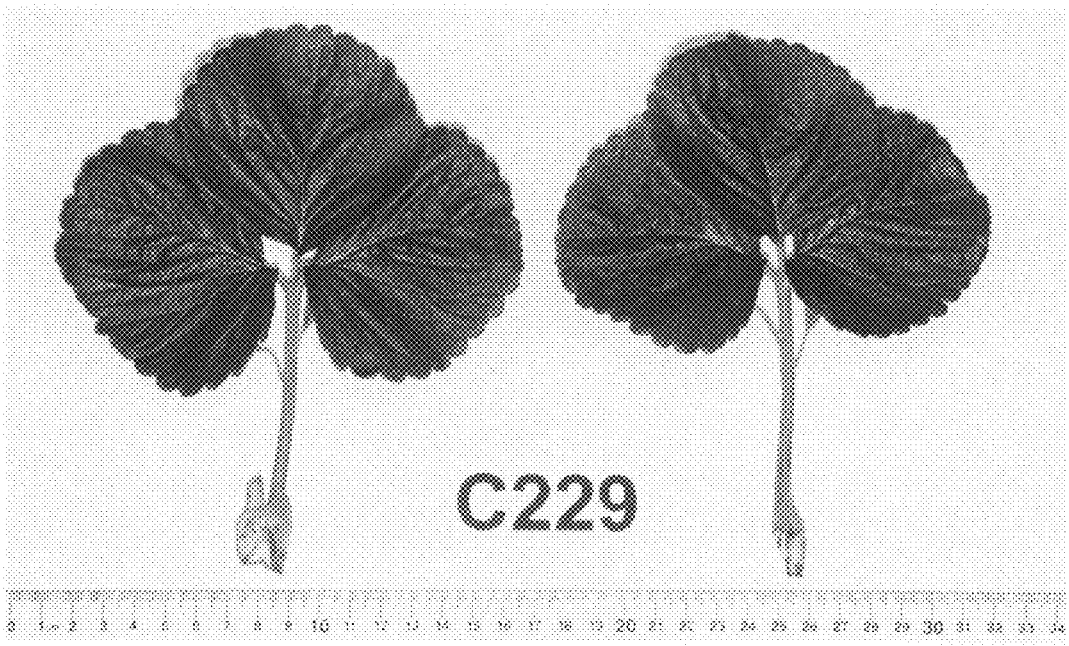
FIG. 2 shows two typical leafs at mid-season.
Figure 3:
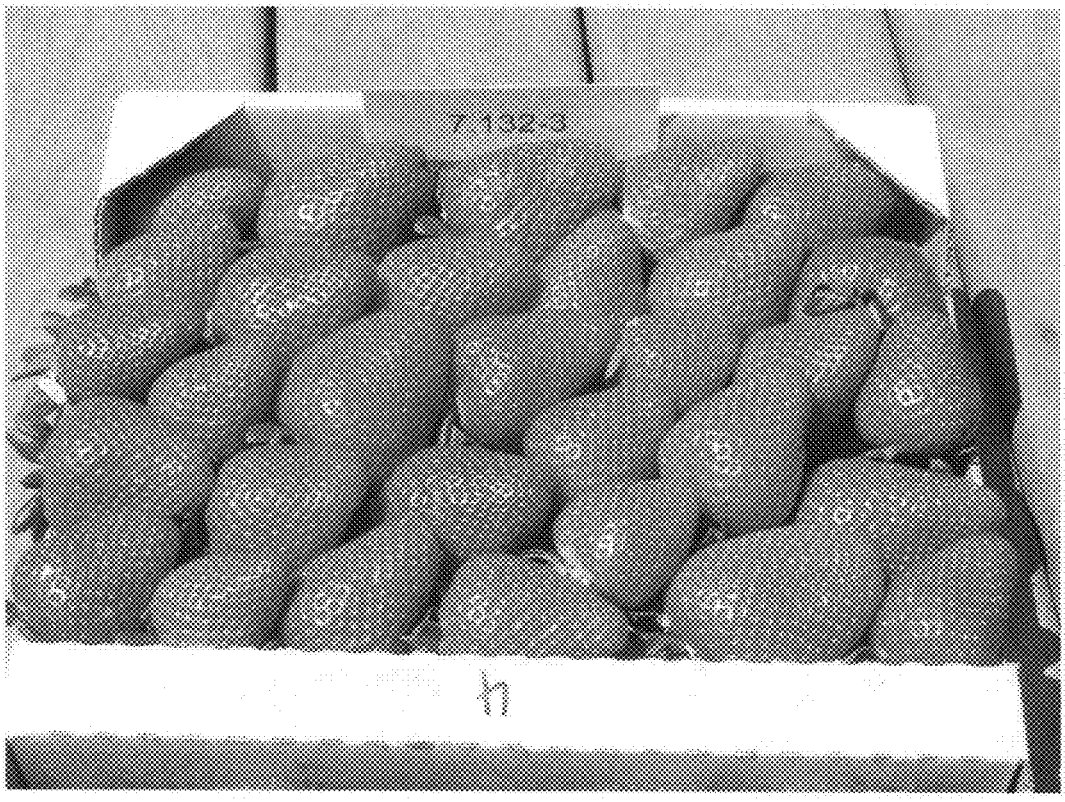
FIG. 3 shows representative mid-season fruit.
Figure 4:
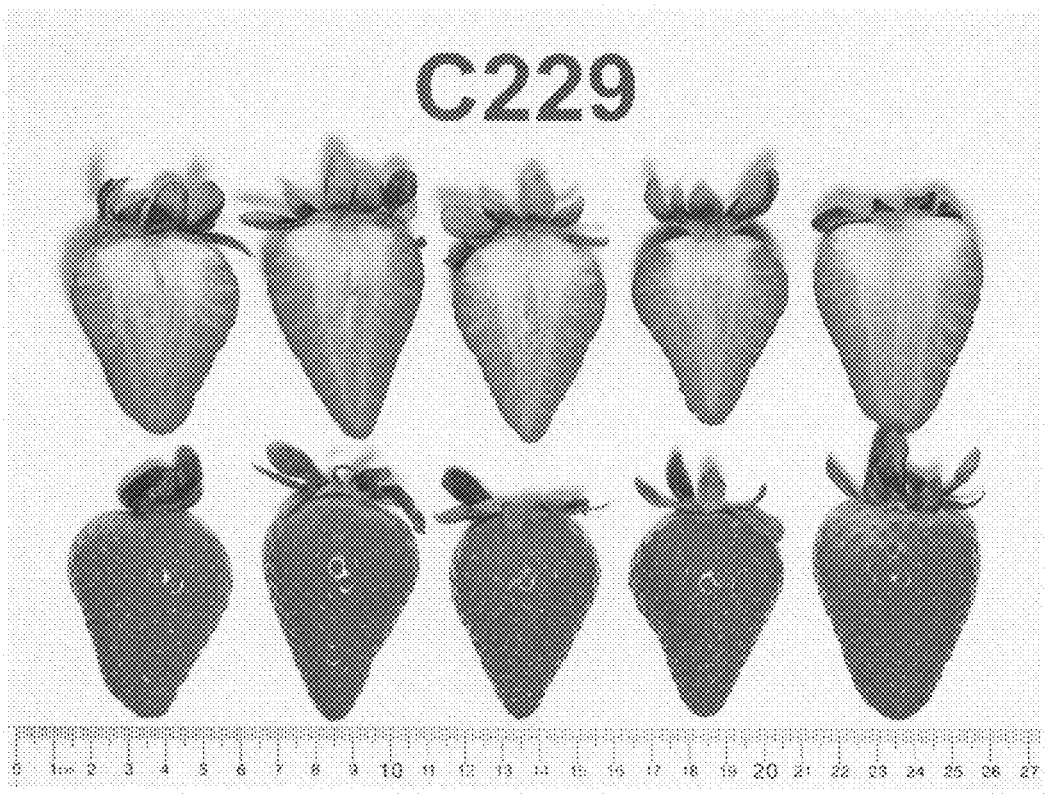
FIG. 4 shows a cross-section of representative mid-season fruit.
Figure 5:
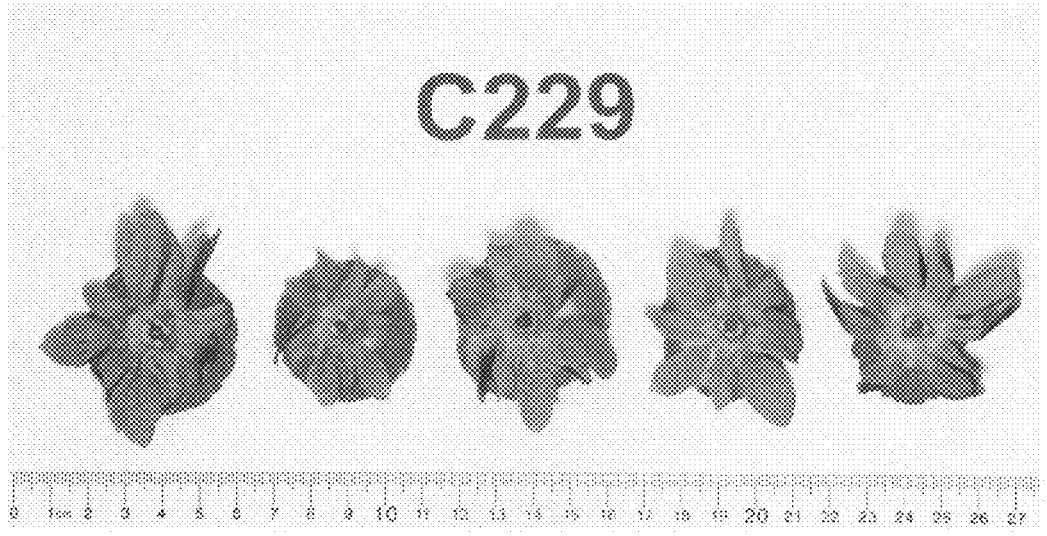
FIG. 5 shows a top-view of representative mid-season fruit.

'Merced' is typical of short-day strawberry cultivars and produces fruit over an extended period when treated appropriately in arid, subtropical climates. The production pattern for 'Merced' is similar to that for 'Camarosa' (U.S. Plant Pat. No. 8,708), although it is somewhat later to initiate fruiting with most cultural treatments. 'Merced' initiates fruiting substantially later than 'Ventana' (U.S. Plant Pat. No. 13,469) and 'Benicia' (U.S. Plant Pat. No. 22,542) when established in very early fall. 'Merced' will be of special interest for winter plantings, where 'Camarosa', 'Ventana', and 'Benicia' have been successful, and in summer plantings where 'Chandler' (U. S. Plant Pat. No. 5,262) and 'Camino Real' (U.S. Plant Pat. No. 13,079) have been successful.

Plants and foliage: With most cultural treatments, fruiting plants of 'Merced' are more open and erect that any of the comparison cultivars, and somewhat smaller than 'Ventana' and 'Benicia' throughout most of the production season. 'Merced' plants are similar in size to 'Camarosa' in most production environments. Comparative statistics of foliar characteristics near mid-season are given for 'Merced' and three comparison cultivars in Table 1. Individual leaflets for 'Merced' are smaller than any of the comparison cultivars, and are less elongated than 'Camarosa' and 'Ventana'. Further, leaves (including petioles) for 'Merced' are slightly shorter than for 'Ventana' and 'Camarosa', and substantially shorter than for 'Benicia'. Petioles for 'Merced' are generally longer and thinner than those of the comparison cultivars. The adaxial (upper) and abaxial (lower) surfaces of leaves for 'Merced' are similar in color to 'Camarosa' and 'Benicia', and darker and less yellow than 'Ventana' leaves at mid-season. Leaves of 'Merced' have consistently more concavity than 'Camarosa', and are similar to those for 'Ventana'. Serrations at mid-season are more pointed than for 'Benicia', but similar in shape and number to 'Ventana' and 'Camarosa'.

TABLE 1

Foliar and plant characteristics for 'Merced', 'Camarosa', 'Ventana', and 'Benicia'.

| | Cultivar | |
|---|---|---|
| Foliar Character | 'Camarosa' | 'Ventana' |
| Plant height (mm) | | |
| mean | 227 | 277 |
| range | 190-320 | 250-300 |
| Plant spread (mm) | | |
| mean | 368 | 425 |
| range | 300-465 | 375-525 |
| Mid-tier leaflet | | |
| Length (mm) | | |
| mean | 85 | 89 |
| range | 70-95 | 80-110 |
| Width (mm) | | |
| mean | 79 | 77 |
| range | 65-90 | 70-90 |
| Mid-tier leaf | | |
| Length (mm) | | |
| mean | 120 | 118 |
| range | 110-140 | 100-140 |
| Width (mm) | | |
| mean | 143 | 153 |
| range | 120-170 | 140-160 |
| Leaf components | | |
| Petiole length (mm) | | |
| mean | 110 | 113 |
| range | 90-150 | 80-120 |
| Petiole diameter (mm) | | |
| mean | 3.6 | 5.3 |
| range | 3-4 | 4-7 |
| Petiolule length (mm) | | |
| mean | 5.1 | 6.9 |
| range | 4-6 | 6-8 |
| # leaflets/leaf | 3 | 3 |
| Leaf convexity | most flat to slight concave | flat to very concave |

TABLE 1-continued

Foliar and plant characteristics for 'Merced', 'Camarosa', 'Ventana', and 'Benicia'.

| | | |
|---|---|---|
| Serrations | | |
| number/leaf | 20.8 | 20.6 |
| range | 19-23 | 18-25 |
| shape | semi-pointed | semi-pointed |
| Leaf pubescence | light-moderate | moderate-heavy |
| Petiole pubescence | | |
| density | heavy | moderate-heavy |
| direction | perpendicular | perpendicular to acropetal |
| Petiole color (Munsell) | | |
| Stipule length (mm) | 2.5 GY 8/9 | 7.5 GY 9/4 |
| mean | 27.2 | 24.0 |
| range | 20-34 | 20-30 |
| Stipule color | | |
| core | 2.5 Y 6/8 | 2.5 GY 8/9 |
| margins | 7.5 Y 6/7 | 5 GY 8/8 |
| Stolon base diameter (mm) | 11.7 | 15.2 |
| Stolons per nursery mother plant | 22.7 | 18.8 |
| Venation | | |
| pattern | pinnate | pinnate |
| color | 7.5 GY 8/7 | 7.5 GY 9/4 |
| | Cultivar | |
| Foliar Character | 'Benicia' | 'Merced' |
| Plant height (mm) | | |
| mean | 245 | 261 |
| range | 220-260 | 240-290 |
| Plant spread (mm) | | |
| mean | 414 | 374 |
| range | 360-500 | 335-400 |
| Mid-tier leaflet | | |
| Length (mm) | | |
| mean | 80 | 76 |
| range | 70-90 | 70-80 |
| Width (mm) | | |
| mean | 80 | 77 |
| range | 75-80 | 70-80 |
| Mid-tier leaf | | |
| Length (mm) | | |
| mean | 128 | 114 |
| range | 110-150 | 90-140 |
| Width (mm) | | |
| mean | 161 | 141 |
| range | 150-180 | 120-160 |
| Leaf components | | |
| Petiole length (mm) | | |
| mean | 136 | 163 |
| range | 110-160 | 140-180 |
| Petiole diameter (mm) | | |
| mean | 4.9 | 4.2 |
| range | 4-6 | 3-5 |
| Petiolule length (mm) | | |
| mean | 5.3 | 8.1 |
| range | 4-6 | 7-9 |
| # leaflets/leaf | 3, rarely 4 or 5 | 3 |
| Leaf convexity | flat to concave | flat to concave |

TABLE 1-continued

Foliar and plant characteristics for 'Merced', 'Camarosa', 'Ventana', and 'Benicia'.

| | | |
|---|---|---|
| Serrations | | |
| number/leaf | 20.5 | 21.0 |
| range | 18-23 | 19-24 |
| shape | Round to semi-pointed | semi-pointed |
| Leaf pubescence | moderate-light | moderate-heavy |
| Petiole pubescence | | |
| density | heavy | moderate-heavy |
| direction | perpendicular | perpendicular |
| Petiole color (Munsell) | | |
| Stipule length (mm) | 7.5 GY 8/10 | 7.5 GY 8/7 |
| mean | 31.1 | 25.1 |
| range | 25-40 | 18-29 |
| Stipule color | | |
| core | 2.5 Y 9/4 | 2.5 GY 8/8 |
| margins | 5 GY 8/8 | 5 GY 8/8 |
| Stolon base diameter (mm) | 16.5 | 10.3 |
| Stolons per nursery mother plant | 22.9 | 12.1 |
| Venation | | |
| pattern | pinnate | pinnate |
| color | 7.5 GY 8/7 | 5 GY 8/8 |

Disease and pest reaction: 'Merced' is moderately resistant to powdery mildew (*Sphaerotheca macularis*), but is moderately susceptible to Anthracnose crown rot (*Colletotrichum acutatum*), and susceptible to *Verticillium* wilt (*Verticillium dahliae*). It is resistant to *Phytophthora* crown rot (*Phytophthora cactorum*) and common leaf spot (*Ramularia tulasnei*) (Table 2). When treated properly, it has tolerance to two-spotted spider mites (*Tetranychus urticae*) equal to that of the comparison cultivars. 'Merced' is tolerant to strawberry viruses encountered in California.

TABLE 2

Disease resistance scores for 'Merced' and three comparison cultivars; *Phytophthora* and *Verticillium* scores were obtained in evaluations conducted in between 2011-2012; *Colletotrichum* was evaluated in 2009.

| Genotype | *Phytophthora* Resistance Score (5 = best) | *Verticillium* Resistance Score (5 = best) | *Colletotrichum* Resistance Score (5 = best) |
|---|---|---|---|
| 'Camarosa' | 3.6 | 3.1 | 2.9 |
| 'Ventana' | 2.5 | 3.1 | 3.2 |
| 'Benicia' | 3.8 | 1.6 | 2.6 |
| 'Merced' | 5.0 | 2.8 | 2.9 |

Flowering, fruiting, fruit, and production characteristics: 'Merced' is similar to other California short-day strawberry cultivars (e. g. 'Ventana', 'Camarosa', and 'Benicia') in that it will flower over an extended period and into spring or summer, given appropriate local temperature and horticultural conditions. With most planting treatments 'Merced' produces fruit later than 'Ventana' and 'Benicia' but earlier than 'Camarosa'. Comparative statistics for flower and fruit characters near mid-season are given for the four cultivars in Table 4. The primary flowers for 'Merced' are similar in size to 'Camarosa', with a calyx that is distinctly larger than the corolla on primary fruit. The flowers are smaller than for 'Benicia' and 'Ventana'. The calyx for 'Merced' varies in position but frequently has a slight indent early in the season. Each primary flower has 6-7 petals, similar to the comparison cultivars on average. The fruit shape for 'Merced' can vary but is typically medium to long conic, which is rarely flattened or slightly obovate. It is easily distinguished by fruit shape from 'Camarosa' (shortened and flattened conic), or 'Ventana' (medium symmetrical conic), and 'Benicia' (often flattened). External and internal fruit color for 'Merced' is lighter than that of 'Camarosa' and 'Benicia', and similar to that of 'Ventana' (Table 3). Achenes vary from yellow to dark red, and are even with the fruit surface or slightly extruded.

'Merced' has been tested under a variety of cultural regimes, and optimal performance is obtained when nursery treatments and nutritional programs similar to those of 'Camarosa', 'Ventana', and 'Benicia' are used. In general, plants of 'Merced' are similar in vigor to 'Camarosa', and less vigorous than 'Ventana' with very early season planting. 'Merced' retains excellent fruit quality in summer planting systems.

When treated with appropriate planting regimes, 'Merced' has larger fruit and produces individual-plant yields greater than any of the comparison cultivars (Table 5). Commercial appearance ratings have also been better than those for all of the comparison cultivars, especially in comparison with 'Camarosa'. Fruit from 'Merced' is substantially firmer than fruit from 'Ventana', but similar in firmness to the other comparison cultivars. Subjectively, 'Merced' has outstanding flavor. The fruit will be exceptional for both fresh market and processing, and will be useful for home gardening purposes.

TABLE 3

Foliar and fruit color characteristics for 'Merced' and three comparison cultivars.

| | Cultivar | | | |
|---|---|---|---|---|
| Color Character | 'Camarosa' | 'Ventana' | 'Benicia' | 'Merced' |
| Leaf color (CIELAB) Adaxial L* | | | | |
| mean | 38.3 | 39.2 | 35.0 | 37.9 |
| range | 37.3-39.8 | 36.0-41.1 | 33.3-36.4 | 35.1-39.2 |
| a* | | | | |
| mean | −12.2 | −14.3 | −11.7 | −13.5 |
| range | −9.5-15.5 | −12.9-16.7 | −10.3-13.5 | −10.9-15.8 |
| b* | | | | |
| mean | 16.9 | 20.6 | 16.9 | 18.1 |
| range | 13.3-19.9 | 17.3-24.8 | 13.1-21.7 | 14.6-20.6 |
| Munsell | 5 GY 5/5 | 2.5 GY 6/8 | 5 GY 5/6 | 5 GY 5/6 |
| Abaxial L* | | | | |
| mean | 52.5 | 53.2 | 48.5 | 50.2 |
| range | 51.3-54.6 | 51.8-54.6 | 41.7-52.3 | 40.0-53.8 |
| a* | | | | |
| mean | −13.1 | −14.2 | −13.5 | −14.0 |
| range | −11.4-14.9 | −13.9-14.7 | −11.9-16.8 | −12.9-15.7 |
| b* | | | | |
| mean | 20.5 | 21.7 | 20.0 | 21.3 |
| range | 18.9-22.4 | 20.3-23.3 | 17.9-21.9 | 19.1-23.8 |
| Munsell | 7.5 GY 8/7 | 10 GY 8/7 | 7.5 GY 5/7 | 10 GY 8/7 |

TABLE 3-continued

Foliar and fruit color characteristics for 'Merced' and three comparison cultivars.

| Color Character | Cultivar 'Camarosa' | 'Ventana' | 'Benicia' | 'Merced' |
|---|---|---|---|---|
| Fruit color (CIELAB) External | | | | |
| L* | | | | |
| mean | 38.6 | 38.1 | 36.0 | 36.9 |
| range | 34.7-42.7 | 37.6-39.0 | 34.2-37.5 | 35.3-39.0 |
| a* | | | | |
| mean | 34.4 | 33.4 | 31.2 | 33.0 |
| range | 33.6-36.2 | 29.4-38.7 | 26.6-36.3 | 30.1-35.1 |
| b* | | | | |
| mean | 22.5 | 19.2 | 14.2 | 16.7 |
| range | 18.8-29.3 | 17.8-21.1 | 10.6-17.3 | 14.2-18.5 |
| Munsell | 7.5 R 4/11 | 5 R 4/12 | 2.5 R 4/0 | 5 R 3/7 |
| Internal | | | | |
| L* | | | | |
| mean | 50.2 | 48.6 | 44.0 | 52.1 |
| range | 46.6-53.3 | 46.2-52.3 | 40.8-47.0 | 45.5-56.6 |
| a* | | | | |
| mean | 30.8 | 28.9 | 30.9 | 24.1 |
| range | 25.6-35.4 | 23.5-33.0 | 27.8-33.6 | 17.9-33.5 |
| b* | | | | |
| mean | 30.1 | 31.3 | 27.5 | 29.8 |
| range | 28.0-32.0 | 30.6-32.5 | 24.6-28.8 | 25.2-33.5 |
| Munsell | 7.5 R 5/13 | 7.5 R 6/13 | 5 R 4/2 | 7.5 R 6/12 |
| Achene color Munsell | 2.5 Y 7/10 | 10 Y 8/11 | 5 R 3/7 | 5 R 3/7 |

TABLE 4

Flower and fruit characteristics for 'Merced' and three comparison cultivars.

| Character | Cultivar 'Camarosa' | 'Ventana' |
|---|---|---|
| Petal number | | |
| mean | 5.8 | 6.2 |
| range | 5-7 | 5-7 |
| Petal shape | | |
| apex | truncate to slightly | truncate to slightly |
| base | obtuse | obtuse |
| margin | attenuate entire | attenuate entire |
| Petal length (mm) | | |
| mean | 11.5 | 13.3 |
| range | 10-13 | 11-15 |
| Petal width (mm) | | |
| mean | 12.0 | 14.6 |
| range | 10-14 | 13-16 |
| Flower position (relative to foliage) | most even some exposed | even to exposed |
| Calyx diam. (mm) | | |
| mean | 40.4 | 47.0 |
| range | 33-47 | 40-50 |

TABLE 4-continued

Flower and fruit characteristics for 'Merced' and three comparison cultivars.

| | | |
|---|---|---|
| Corolla diam. (mm) | | |
| mean | 26.1 | 39.0 |
| range | 23-31 | 35-45 |
| Sepal length (mm) | | |
| mean | 14.3 | 16.6 |
| range | 12-18 | 14-19 |
| Sepal width (mm) | | |
| mean | 8.3 | 8.4 |
| range | 7-10 | 7-10 |
| Sepal color (Munsell) | 5 GY 7/10 | 5 GY 5/5 |
| Pedicel length (mm) | | |
| mean | 155 | 115 |
| range | 130-180 | 90-140 |
| Pedicel diameter (mm) | | |
| mean | 2.7 | 3.5 |
| range | 2-4 | 3-4 |
| Pedicel color | 7.5 GY 8/7 | 5 GY 8/9 |
| Fruit shape | | |
| Fruit length (mm) | | |
| mean | 46.0 | 48.4 |
| range | 40-48 | 47-52 |
| Fruit width (mm) | | |
| mean | 37.4 | 42.6 |
| range | 33-46 | 40-46 |
| Length/width | | |
| ratio | 1.26 | 1.17 |
| range | 1.0-1.4 | 1.1-1.2 |
| subjective | Obovate-flat | Medium conic |
| Primary/secondary fruit comparison | | |
| size (subjective) | 50-70% | 55-75% |
| shape | similar shape, more conic | similar shape |
| Extent/size of hollow core | small-absent | Small |
| Calyx | | |
| position | indented-neck | indent-reflexed |
| size relative to fruit | equal or less than fruit diameter | equal or less than fruit diameter |
| Seed position | indented-extruded | mostly even |
| Adherence of Calyx to Fruit | Weak | Intermediate |

| Character | Cultivar 'Benicia' | 'Merced' |
|---|---|---|
| Petal number | | |
| mean | 6.1 | 5.9 |
| range | 5-7 | 5-7 |
| Petal shape | | |
| apex | truncate to slightly | truncate to slightly |
| base | obtuse | obtuse |
| margin | attenuate entire | attenuate entire |

TABLE 4-continued

Flower and fruit characteristics for 'Merced' and three comparison cultivars.

| | | |
|---|---|---|
| Petal length (mm) | | |
| mean | 11.7 | 13.6 |
| range | 8-13 | 10-15 |
| Petal width (mm) | | |
| mean | 14.4 | 14.9 |
| range | 8-13 | 12-16 |
| Flower position (relative to foliage) | even to exposed | even to exposed |
| Calyx diam. (mm) | | |
| mean | 50.8 | 39.1 |
| range | 47-53 | 33-45 |
| Corolla diam. (mm) | | |
| mean | 39.6 | 27.4 |
| range | 39-41 | 24-31 |
| Sepal length (mm) | | |
| mean | 16.4 | 13.5 |
| range | 13-20 | 10-17 |
| Sepal width (mm) | | |
| mean | 8.4 | 8.0 |
| range | 7-10 | 6-9 |
| Sepal color (Munsell) | 10 GY 8/7 | 7.5 GY 4/4 |
| Pedicel length (mm) | | |
| mean | 183 | 185 |
| range | 150-210 | 150-220 |
| Pedicel diameter (mm) | | |
| mean | 3.7 | 3.5 |
| range | 3-5 | 2-5 |
| Pedicel color | 2.5 GY 8/9 | 2.5 GY 9/8 |
| Fruit shape | | |
| Fruit length (mm) | | |
| mean | 46.5 | 52.3 |
| range | 41-52 | 49-62 |
| Fruit width (mm) | | |
| mean | 42.4 | 47.4 |
| range | 36-46 | 43-54 |

TABLE 4-continued

Flower and fruit characteristics for 'Merced' and three comparison cultivars.

| | | |
|---|---|---|
| Length/width | | |
| ratio | 1.08 | 1.15 |
| range | 1.0-1.2 | 1.0-1.2 |
| subjective | Medium conic | Medium-long conic |
| Primary/secondary fruit comparison | | |
| size (subjective) | 55-65% | 60-75% |
| shape | similar shape | similar shape |
| Extent/size of hollow core | small-absent | small-absent |
| Calyx | | |
| position | even-indented | even-reflexed |
| size relative to fruit | equal or greater than fruit diameter | equal or greater than fruit diameter |
| Seed position | even-indented | even-extruded |
| Adherence of Calyx to Fruit | Weak | Weak |

Flower and plant measurements were obtained in April 2012. Fruit measurements were obtained in between May 10-20, 2012.

TABLE 5

Performance of 'Merced' and three comparison cultivars were evaluated in Watsonville, CA, in between 2010-12. All plants for these trials were harvested from a commercial nursery near Macdoel, CA, in between October 15-16, and transplanted after 6-7 days to supplemental storage. Fruit harvest was initiated in early April and continued through the last week of August. (52" 2-row beds, 17,300 plants/acre).

| Item | Yield (g/plant) | Appearance Score (5 = best) | Fruit Size (g/fruit) | Firmness |
|---|---|---|---|---|
| 'Camarosa' | 1,960 | 2.9 | 28.5 | 11.7 |
| 'Ventana' | 2,112 | 3.2 | 31.3 | 10.4 |
| 'Benicia' | 1,959 | 3.5 | 34.2 | 11.1 |
| 'Merced' | 2,339 | 4.3 | 35.0 | 11.9 |

What is claimed is:

1. A new and distinct cultivar of strawberry plant having the characteristics substantially as described and illustrated herein.

* * * * *